United States Patent
Gao et al.

(10) Patent No.: US 11,391,683 B2
(45) Date of Patent: Jul. 19, 2022

(54) METHOD TO DETERMINE PORE SIZE DISTRIBUTION OF ROCKS WITH ROUGH SURFACE FROM CAPILLARY PRESSURE BY NUCLEAR MAGNETIC RESONANCE

(71) Applicant: SAUDI ARABIAN OIL COMPANY, Dhahran (SA)

(72) Inventors: Jun Gao, Dhahran (SA); Hyung Tae Kwak, Dhahran (SA); Marwah M. Alsinan, Al Qatif (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 146 days.

(21) Appl. No.: 16/894,029

(22) Filed: Jun. 5, 2020

(65) Prior Publication Data
US 2021/0381993 A1 Dec. 9, 2021

(51) Int. Cl.
*G01R 33/44* (2006.01)
*G01N 24/08* (2006.01)
(Continued)

(52) U.S. Cl.
CPC ....... *G01N 24/081* (2013.01); *G01N 15/0806* (2013.01); *G01N 15/088* (2013.01);
(Continued)

(58) Field of Classification Search
CPC ............. G01N 24/081; G01N 15/0806; G01N 15/088; G01N 33/24; G01N 24/10;
(Continued)

(56) References Cited

U.S. PATENT DOCUMENTS 4,728,892 A 3/1988 Vinegar et al.
6,008,645 A 12/1999 Bowers et al.
(Continued)

FOREIGN PATENT DOCUMENTS

WO 2019090316 A1 5/2019
WO 2019199304 A1 10/2019

OTHER PUBLICATIONS

Lyu Chaohui et al, "Application of NMR T2 to Pore Size Distribution and Movable Fluid Distribution in Tight Sandstones", Energy & Fuels, vol. 32; No. 2; Feb. 15, 2018; pp. 1395-1405 (11 pages).
(Continued)

*Primary Examiner* — Jermele M Hollington
*Assistant Examiner* — Taqi R Nasir
(74) *Attorney, Agent, or Firm* — Osha Bergman Watanabe & Burton LLP

(57) ABSTRACT

A method for determining pore size distribution of rocks is provided. Capillary pressure measurements on rock cores are analyzed to determine a pore size distribution, with smaller pores requiring greater capillary pressure to relinquish contained fluid. Large pores with rough surfaces introduce inaccuracies in determining the pore size distribution. Embodiments of the invention correct the rough surface induced inaccuracies by measuring the shift in NMR T2 distribution from full saturation to the current state of desaturation and subtracting the T2 contributions in the desaturated state that have smaller T2 values (i.e., smaller transverse relaxation time) than the smallest T2 values (i.e., shortest transverse relaxation time) in the saturated distribution.

20 Claims, 6 Drawing Sheets

(51) Int. Cl.
*G01N 15/08* (2006.01)
*G01N 33/24* (2006.01)
*G01V 3/32* (2006.01)

(52) U.S. Cl.
CPC ............. *G01N 33/24* (2013.01); *G01R 33/44* (2013.01); *G01V 3/32* (2013.01)

(58) Field of Classification Search
CPC ................. G01R 33/44; G01R 33/543; G01R 33/5608; G01R 33/4828; G01R 33/3415; G01R 33/283; G01R 33/307; G01R 33/60; G01V 3/32; E21B 49/08; E21B 2049/085
See application file for complete search history.

(56) References Cited

U.S. PATENT DOCUMENTS

| | | | |
|---|---|---|---|
| 10,247,684 | B2 | 4/2019 | Valori et al. |
| 2003/0057947 | A1 | 3/2003 | Ni et al. |
| 2010/0237860 | A1* | 9/2010 | Hurlimann ....... G01R 33/56341 324/303 |
| 2012/0241149 | A1 | 9/2012 | Chen et al. |
| 2013/0057277 | A1 | 3/2013 | Zielinski et al. |
| 2014/0055134 | A1 | 2/2014 | Fordham et al. |
| 2014/0132259 | A1 | 5/2014 | Song |
| 2014/0257702 | A1 | 9/2014 | Al-Ibrahim et al. |
| 2015/0346377 | A1* | 12/2015 | Jebutu ..................... E21B 49/00 324/303 |
| 2016/0139066 | A1* | 5/2016 | Luo .......................... G01V 3/32 324/318 |
| 2018/0003786 | A1* | 1/2018 | Washburn .............. G01N 23/04 |

OTHER PUBLICATIONS

Li Chaozheng et al, "Analysis of Petrophysical Characteristics and Water Movability of Tight Sandstone Using Low-Field Nuclear Magnetic Resonance", Natural Resources Research, Springer US, Boston; vol. 29; No. 4; Nov. 2, 2019, pp. 2547-2573 (27 pages).
International Search Report and Written Opinion issued in corresponding International Patent Application No. PCT/US2020/047144, dated Feb. 26, 2021 (15 pages).
Chen, Quan and Bruce J. Balcom, "Calillary Pressure Curve Measurement Using a Single-Moderate-Speed Centrifuge and Quantitative Magnetic Resonance Imaging", SCA2005-44, International Symposium of the Society of Core Analysts, Aug. 2005 (12 pages).
Coates, G.R. et al., "A New Characterization of Bulk-Volume Irreducible Using Magnetic Resonance", The Log Analyst, Jan.-Feb. 1998, pp. 51-63 (13 pages).

\* cited by examiner

METHOD TO DETERMINE PORE SIZE DISTRIBUTION OF ROCKS WITH ROUGH SURFACE FROM CAPILLARY PRESSURE BY NUCLEAR MAGNETIC RESONANCE

BACKGROUND

Hydrocarbon fluids in microscopic spaces in porous reservoir sedimentary rocks flow to the wellbore for extraction during production. Accurate quantification of such microscopic spaces is essential to understand the rock storage capacity and ability for the fluids to flow during production operations. These spaces consist of microscopic and interconnected pores that are formed during deposition and subsequently modified by diagenesis. Methods based on geometry and/or capillary pressures are used to measure the pore size distribution in porous reservoir sedimentary rocks.

SUMMARY

In general, in one aspect, the invention relates to a method for determining a pore size distribution in a rock sample. The method includes saturating the rock sample with a fluid, acquiring a first set of nuclear magnetic resonance (NMR) measurements of the rock sample, generating, by a computer processor and based on a first T2 distribution of the first set of NMR measurements, a first saturation measure, the first saturation measure representing an initial amount of the fluid stored in the rock sample, applying, subsequent to acquiring the first set of NMR measurements, a first external force to the rock sample to expel the fluid from a first plurality of pores of the rock sample, acquiring, subsequent to applying the first external force, a second set of NMR measurements of the rock sample, identifying, by the computer processor based on comparing a second T2 distribution of the second set of NMR measurements and the first T2 distribution, a portion of the second T2 distribution that corresponds to the fluid remaining on interior surfaces of the first plurality of pores, generating, by the computer processor and based on the second T2 distribution and excluding the identified portion, a second saturation measure of the rock sample, the second saturation measure representing a remaining amount of the fluid remained in a second plurality of pores of the rock sample, and determining, by the computer processor and based at least on the first saturation measure and the second saturation measure, the pore size distribution.

In general, in one aspect, the invention relates to a computer system for determining a pore size distribution in a rock sample. The system includes a processor and a memory coupled to the processor. The memory storing instructions, when executed, include functionality for acquiring a first set of nuclear magnetic resonance (NMR) measurements of a rock sample saturated with a fluid, wherein a first external force is applied, subsequent to acquiring the first set of NMR measurements, to the rock sample to expel the fluid from a first plurality of pores of the rock sample, generating, based on a first T2 distribution of the first set of NMR measurements, a first saturation measure, the first saturation measure representing an initial amount of the fluid stored in the rock sample, acquiring, subsequent to applying the first external force, a second set of NMR measurements of the rock sample, identifying, by comparing a second T2 distribution of the second set of NMR measurements and the first T2 distribution, a portion of the second T2 distribution that corresponds to the fluid remaining on interior surfaces of the first plurality of pores, generating, based on the second T2 distribution and excluding the identified portion, a second saturation measure of the rock sample, the second saturation measure representing a remaining amount of the fluid remained in a second plurality of pores of the rock sample, and determining, based at least on the first saturation measure and the second saturation measure, the pore size distribution.

In general, in one aspect, the invention relates to a non-transitory computer readable medium storing instructions executable by a computer processor for determining a pore size distribution in a rock sample. The instructions, when executed by the computer processor, include functionality for acquiring a first set of nuclear magnetic resonance (NMR) measurements of a rock sample saturated with a fluid, wherein a first external force is applied, subsequent to acquiring the first set of NMR measurements, to the rock sample to expel the fluid from a first plurality of pores of the rock sample, generating, based on a first T2 distribution of the first set of NMR measurements, a first saturation measure, the first saturation measure representing an initial amount of the fluid stored in the rock sample, acquiring, subsequent to applying the first external force, a second set of NMR measurements of the rock sample, identifying, by comparing a second T2 distribution of the second set of NMR measurements and the first T2 distribution, a portion of the second T2 distribution that corresponds to the fluid remaining on interior surfaces of the first plurality of pores, generating, based on the second T2 distribution and excluding the identified portion, a second saturation measure of the rock sample, the second saturation measure representing a remaining amount of the fluid remained in a second plurality of pores of the rock sample, and determining, based at least on the first saturation measure and the second saturation measure, the pore size distribution.

Other aspects and advantages will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1:
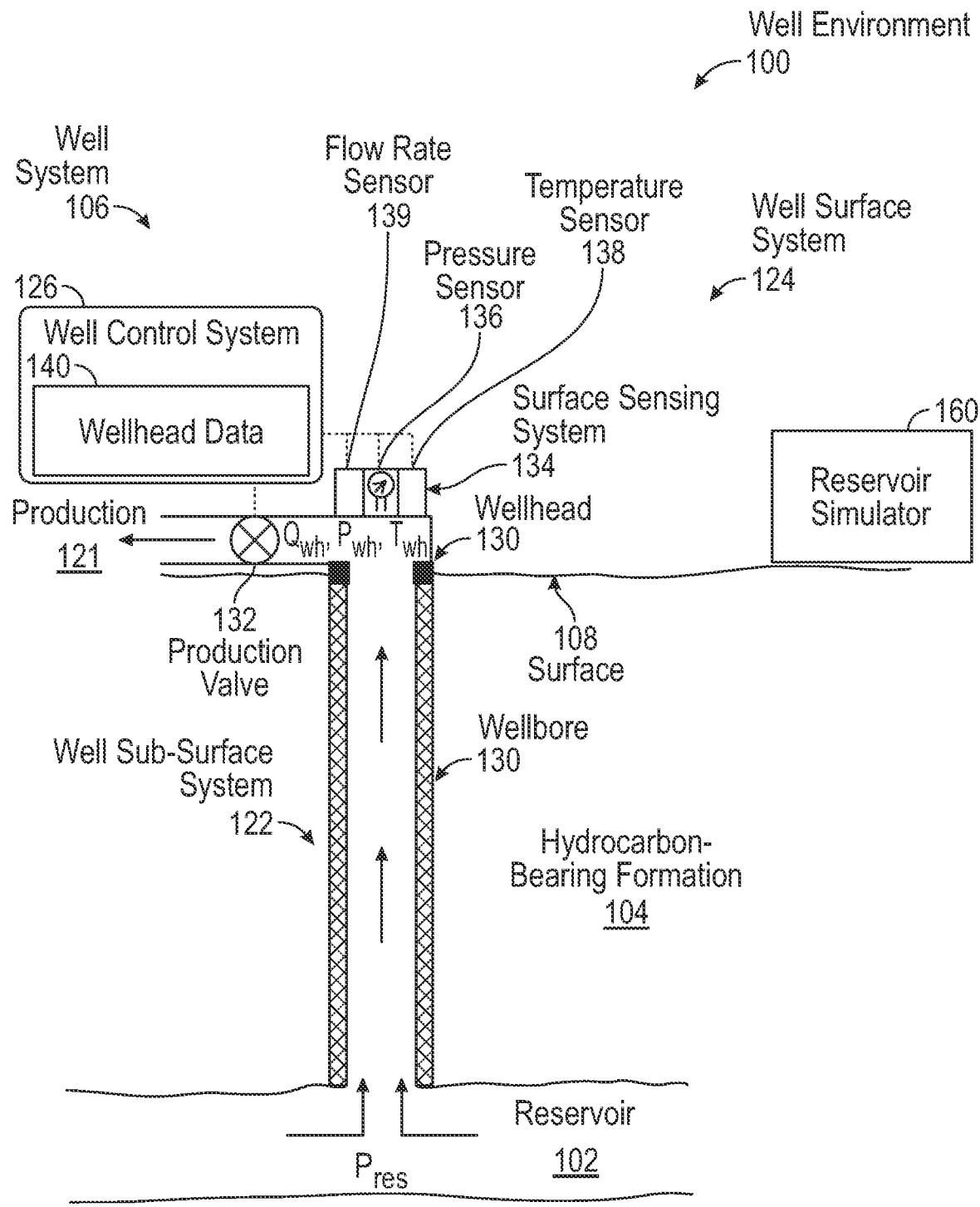
FIGS. 1, 2, 3, and 4 show systems in accordance with one or more embodiments.

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Embodiments of the invention provide a method, a system, and a non-transitory computer readable medium for determining pore size distribution of rocks with rough pore surfaces using capillary pressure measurements based on a nuclear magnetic resonance (NMR) method. Capillary pressure measurements on rock cores are analyzed to determine a pore size distribution, with smaller pores requiring greater capillary pressure to relinquish contained fluid. Some measurements, for example, in the mercury injection method, uses pore throat size as a proxy for pore size. The NMR method, on the other hand, yields the surface-to-volume ratio of a (water-wet) pore as a representation of pore size. The NMR method measures a transverse relaxation time (T2) distribution when surface relaxivity p is known. However, large pores with rough surfaces introduce inaccuracies in determining the pore size distribution. Embodiments of the invention correct the rough surface induced inaccuracies by measuring the shift in T2 distribution from full saturation to the current state of desaturation and subtracting the T2 contributions in the desaturated state that have smaller T2 values (i.e., smaller transverse relaxation time) than the smallest T2 values (i.e., shortest transverse relaxation time) in the saturated distribution.

Turning to FIG. 1, FIG. 1 shows a schematic diagram in accordance with one or more embodiments. As shown in FIG. 1, FIG. 1 illustrates a well environment (100) that includes a hydrocarbon reservoir ("reservoir") (102) located in a subsurface hydrocarbon-bearing formation ("formation") (104) and a well system (106). The hydrocarbon-bearing formation (104) may include a porous or fractured rock formation that resides underground, beneath the earth's surface ("surface") (108). In the case of the well system (106) being a hydrocarbon well, the reservoir (102) may include a portion of the hydrocarbon-bearing formation (104). The hydrocarbon-bearing formation (104) and the reservoir (102) may include different layers of rock having varying characteristics, such as varying degrees of permeability, porosity, capillary pressure, and resistivity. In the case of the well system (106) being operated as a production well, the well system (106) may facilitate the extraction of hydrocarbons (or "production") from the reservoir (102).

In some embodiments, the well system (106) includes a wellbore (120), a well sub-surface system (122), a well surface system (124), and a well control system ("control system") (126). The control system (126) may control various operations of the well system (106), such as well production operations, well completion operations, well maintenance operations, and reservoir monitoring, assessment and development operations. In some embodiments, the control system (126) includes a computer system that is the same as or similar to that of computer system (700) described below in FIGS. 7A and 7B and the accompanying description.

The wellbore (120) may include a bored hole that extends from the surface (108) into a target zone of the hydrocarbon-bearing formation (104), such as the reservoir (102). An upper end of the wellbore (120), terminating at or near the surface (108), may be referred to as the "up-hole" end of the wellbore (120), and a lower end of the wellbore, terminating in the hydrocarbon-bearing formation (104), may be referred to as the "down-hole" end of the wellbore (120). The wellbore (120) may facilitate the circulation of drilling fluids during drilling operations, the flow of hydrocarbon production ("production") (121) (e.g., oil and gas) from the reservoir (102) to the surface (108) during production operations, the injection of substances (e.g., water) into the hydrocarbon-bearing formation (104) or the reservoir (102) during injection operations, or the communication of monitoring devices (e.g., logging tools) into the hydrocarbon-bearing formation (104) or the reservoir (102) during monitoring operations (e.g., during in situ logging operations).

In some embodiments, during operation of the well system (106), the control system (126) collects and records wellhead data (140) for the well system (106). The wellhead data (140) may include, for example, a record of measurements of wellhead pressure ($P_{wh}$) (e.g., including flowing wellhead pressure), wellhead temperature ($T_{wh}$) (e.g., including flowing wellhead temperature), wellhead production rate ($Q_{wh}$) over some or all of the life of the well (106), and water cut data. In some embodiments, the measurements are recorded in real-time, and are available for review or use within seconds, minutes or hours of the condition being sensed (e.g., the measurements are available within 1 hour of the condition being sensed). In such an embodiment, the wellhead data (140) may be referred to as "real-time" wellhead data (140). Real-time wellhead data (140) may enable an operator of the well (106) to assess a relatively current state of the well system (106), and make real-time decisions regarding development of the well system (106) and the reservoir (102), such as on-demand adjustments in regulation of production flow from the well.

In some embodiments, the well sub-surface system (122) includes casing installed in the wellbore (120). For example, the wellbore (120) may have a cased portion and an uncased (or "open-hole") portion. The cased portion may include a portion of the wellbore having casing (e.g., casing pipe and casing cement) disposed therein. The uncased portion may include a portion of the wellbore not having casing disposed therein. In some embodiments, the casing includes an annular casing that lines the wall of the wellbore (120) to define a central passage that provides a conduit for the transport of tools and substances through the wellbore (120). For example, the central passage may provide a conduit for lowering logging tools into the wellbore (120), a conduit for the flow of production (121) (e.g., oil and gas) from the reservoir (102) to the surface (108), or a conduit for the flow of injection substances (e.g., water) from the surface (108) into the hydrocarbon-bearing formation (104). In some embodiments, the well sub-surface system (122) includes production tubing installed in the wellbore (120). The production tubing may provide a conduit for the transport of tools and substances through the wellbore (120). The production tubing may, for example, be disposed inside casing. In such an embodiment, the production tubing may provide a conduit for some or all of the production (121) (e.g., oil and gas) passing through the wellbore (120) and the casing.

In some embodiments, the well surface system (124) includes a wellhead (130). The wellhead (130) may include a rigid structure installed at the "up-hole" end of the wellbore (120), at or near where the wellbore (120) terminates at the Earth's surface (108). The wellhead (130) may include structures for supporting (or "hanging") casing and production tubing extending into the wellbore (120). Production (121) may flow through the wellhead (130), after exiting the wellbore (120) and the well sub-surface system (122), including, for example, the casing and the production tubing. In some embodiments, the well surface system (124) includes flow regulating devices that are operable to control the flow of substances into and out of the wellbore (120). For example, the well surface system (124) may include one or more production valves (132) that are operable to control the flow of production (134). For example, a production valve (132) may be fully opened to enable unrestricted flow of production (121) from the wellbore (120), the production valve (132) may be partially opened to partially restrict (or "throttle") the flow of production (121) from the wellbore (120), and production valve (132) may be fully closed to fully restrict (or "block") the flow of production (121) from the wellbore (120), and through the well surface system (124).

In some embodiments, the wellhead (130) includes a choke assembly. For example, the choke assembly may include hardware with functionality for opening and closing the fluid flow through pipes in the well system (106). Likewise, the choke assembly may include a pipe manifold that may lower the pressure of fluid traversing the wellhead. As such, the choke assembly may include set of high pressure valves and at least two chokes. These chokes may be fixed or adjustable or a mix of both. Redundancy may be provided so that if one choke has to be taken out of service, the flow can be directed through another choke. In some embodiments, pressure valves and chokes are communicatively coupled to the well control system (126). Accordingly, a well control system (126) may obtain wellhead data regarding the choke assembly as well as transmit one or more commands to components within the choke assembly in order to adjust one or more choke assembly parameters.

Keeping with FIG. 1, in some embodiments, the well surface system (124) includes a surface sensing system (134). The surface sensing system (134) may include sensors for sensing characteristics of substances, including production (121), passing through or otherwise located in the well surface system (124). The characteristics may include, for example, pressure, temperature and flow rate of production (121) flowing through the wellhead (130), or other conduits of the well surface system (124), after exiting the wellbore (120).

In some embodiments, the surface sensing system (134) includes a surface pressure sensor (136) operable to sense the pressure of production (151) flowing through the well surface system (124), after it exits the wellbore (120). The surface pressure sensor (136) may include, for example, a wellhead pressure sensor that senses a pressure of production (121) flowing through or otherwise located in the wellhead (130). In some embodiments, the surface sensing system (134) includes a surface temperature sensor (138) operable to sense the temperature of production (151) flowing through the well surface system (124), after it exits the wellbore (120). The surface temperature sensor (138) may include, for example, a wellhead temperature sensor that senses a temperature of production (121) flowing through or otherwise located in the wellhead (130), referred to as "wellhead temperature" ($T_{wh}$). In some embodiments, the surface sensing system (134) includes a flow rate sensor (139) operable to sense the flow rate of production (151) flowing through the well surface system (124), after it exits the wellbore (120). The flow rate sensor (139) may include hardware that senses a flow rate of production (121) ($Q_{wh}$) passing through the wellhead (130).

In some embodiments, the well system (106) includes a reservoir simulator (160). For example, the reservoir simulator (160) may include hardware and/or software with functionality for generating one or more reservoir models regarding the hydrocarbon-bearing formation (104) and/or performing one or more reservoir simulations. For example, the reservoir simulator (160) may store well logs and data regarding core samples for performing simulations. A reservoir simulator may further analyze the well log data, the core sample data, seismic data, and/or other types of data to generate and/or update the one or more reservoir models. While the reservoir simulator (160) is shown at a well site, embodiments are contemplated where reservoir simulators are located away from well sites. In some embodiments, the reservoir simulator (160) may include a computer system that is similar to the computer system (800) described below with regard to FIGS. 7A and 7B and the accompanying description.

Keeping with reservoir simulators, a reservoir simulator may include functionality for solving well equations and reservoir equations separately, e.g., using Additive Schwartz methods. When the number of wells in a simulation is relatively small, computation time spent solving well equations may be a small fraction of the total computation time. However, in massive full-field simulations, where hundreds or thousands of wells are being simulated, the total computation time for solving well equations may increase considerably. This may be particularly true when a multi-segment well model is used as the number of unknown well parameters to be solved may be much larger than a conventional well model. As such, reservoir simulators may assign wells to computer processes in parallel computing tasks statically and/or dynamically. For example, at the beginning of a reservoir simulation, a well may be assigned to a single computer process that performs the computations necessary for this well. In some embodiments, placement of a well within a computer process may be independent of grid partitioning, e.g., whether the well is surrounded by fine-grid cells or coarsened grid blocks. During a simulation, a computer process may access both grid data for a reservoir model and well data. As such, well assignment may affect such parallel communication patterns and thereby may influence reservoir simulation performance.

In some embodiments, well assignment for parallel computer processes may include the case where a number of wells being simulated is greater than the number of computer processes involved in a reservoir simulation. Thus, multiple wells may be assigned to one computer process operating within a parallel processing stage. As wells may not need to be solved at all times during a reservoir simulation, e.g., only when the wells are producing or injecting, a situation may occur where one computer process is solving equations for multiple wells while a production well assigned to another computer process is inactive causing the computer process to be idle (i.e., waiting for the other computer processes to finish in the parallel processing stage).

Figure 2:
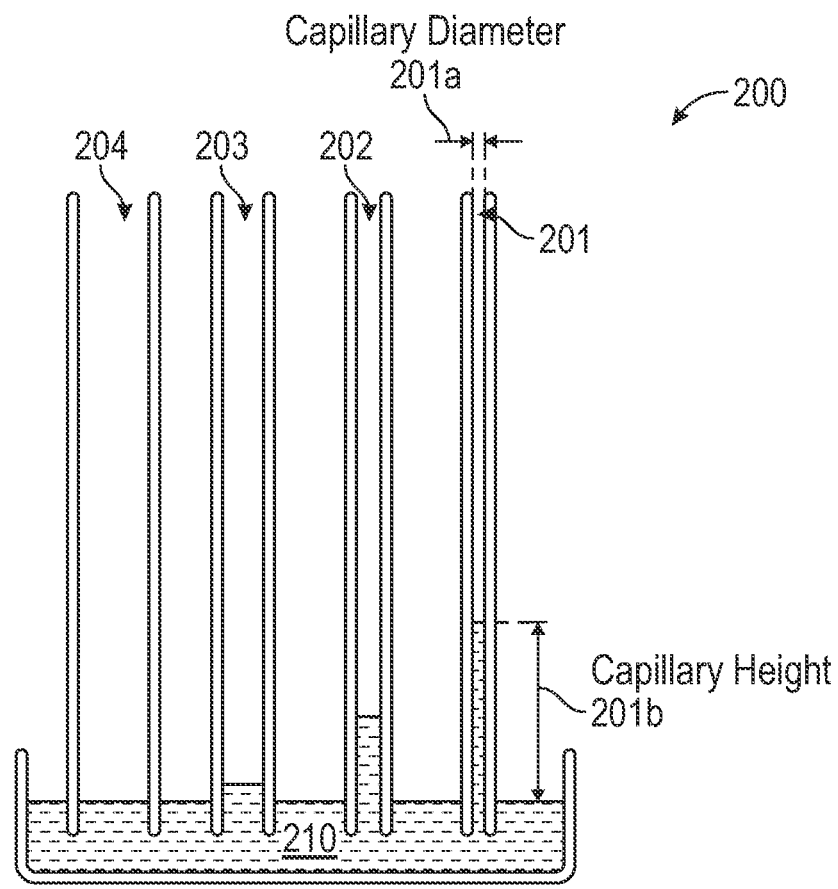

Turning to FIG. 2, FIG. 2 shows a schematic diagram in accordance with one or more embodiments. In one or more embodiments, one or more of the modules and/or elements shown in FIG. 2 may be omitted, repeated, and/or substituted. Accordingly, embodiments of the invention should not be considered limited to the specific arrangements of modules and/or elements shown in FIG. 2.

As shown in FIG. 2, FIG. 2 illustrates a capillary bundle model (200) of a porous media (e.g., a sedimentary rock in a reservoir). In particular, the capillary bundle model (200) approximates the pore spaces in the sedimentary rock (e.g., from a core sample of the reservoir) as aligned, separate capillary tubes (e.g., capillary tubes (201), (202), (203, (204)) in a fluid tank. The core sample saturated with a fluid (210) in the pore spaces is modeled as the fluid tank containing the fluid (210). Although four capillary tubes are shown in FIG. 2, the capillary bundle model (200) may include many more capillary tubes arranged in different configurations. Specifically, the capillary tube (201) represents a particular pore space where the capillary diameter (201a) represents a pore size and the capillary height (201b) represents a capillary pressure of the pore space in the core sample. In the capillary bundle model (200), the capillary pressure, reflected by the capillary height (201b), is related to the capillary diameter (201a) by the equation (Young-Laplace) below:

$$P_c = \rho g h = \frac{2\sigma \cos\theta}{R} \qquad \text{Eq. (1)}$$

In the equation Eq. (1), Pc denotes the capillary pressure, σ denotes an interfacial tension, θ denotes a contact angle, R denotes the capillary radius or half of the capillary diameter, ρ denotes the density of the fluid (210), g denotes the gravitational constant, and h denotes the capillary height.

Based on the equation Eq. (1) above, the capillary bundle model (200) is used to model the pore size distribution in the core sample based on capillary pressure measurements of the core sample. The pore size distribution is a distribution function that specifies a tally of pore spaces with respect to the corresponding pore size over a range of pore sizes found in the core sample. For example, the tally may be expressed in an actual count, a percentage, a probability, or other type of measures. In the capillary bundle model (200), each of the capillary tubes (201), (202), (203), and (204) represents one pore and contributes one count to the pore size distribution.

Various methods may be used to physically measure the capillary pressure of the core sample. The methods include a porous plate method, a centrifuge method, and a mercury injection method. In each method, a core sample saturated with a particular fluid is invaded by another fluid under an applied external force to expel the particular fluid from the pore spaces. For example, the external force in the porous plate method is the gas pressure pressing the core sample against a porous plate where both the core sample and the porous plate are saturated with fluid. The external force in the centrifuge method is the centrifugal force created by spinning the saturated core sample around a rotation axis where the core sample is immersed in a different fluid. The external force in the mercury injection method is the pressure that forces the mercury to enter the saturated core sample. For each of these methods, at a hydrostatic equilibrium condition, the external force is counterbalanced by the capillary pressure in the core sample. For example, under the lowest level of the applied external force, the fluid may be expelled from larger pores represented by the capillary tube (204) but remains in the smaller pores represented by the capillary tubes (201), (202), and (203). Under an increased level of the applied external force, the fluid may be further expelled from pores represented by the capillary tube (203) but remains in the still smaller pores represented by the capillary tubes (201) and (202). The external force is applied with multiple incremented levels to record a relationship between the amount of fluid expelled from the core sample versus the applied external force. In the context that the external force is counterbalanced by the capillary pressure, the recorded relationship is referred to as the capillary pressure curve. At each hydrostatic equilibrium condition of the applied external force levels, the amount of the expelled fluid may be physically measured. Alternatively, a nuclear magnetic resonance (NMR) method is applied to the core sample to estimate the amount of fluid remaining in the core sample. The amount of the expelled fluid can be calculated by subtracting the remaining amount of the fluid from the initial amount of the fluid in the core sample.

In each of the methods described above, the measured capillary pressure curve is analyzed based on the capillary bundle model (e.g., capillary bundle model (200)) to generate the pore size distribution of the core sample. Details of measuring the capillary pressure curve and generating the pore size distribution are described below.

Figure 3:
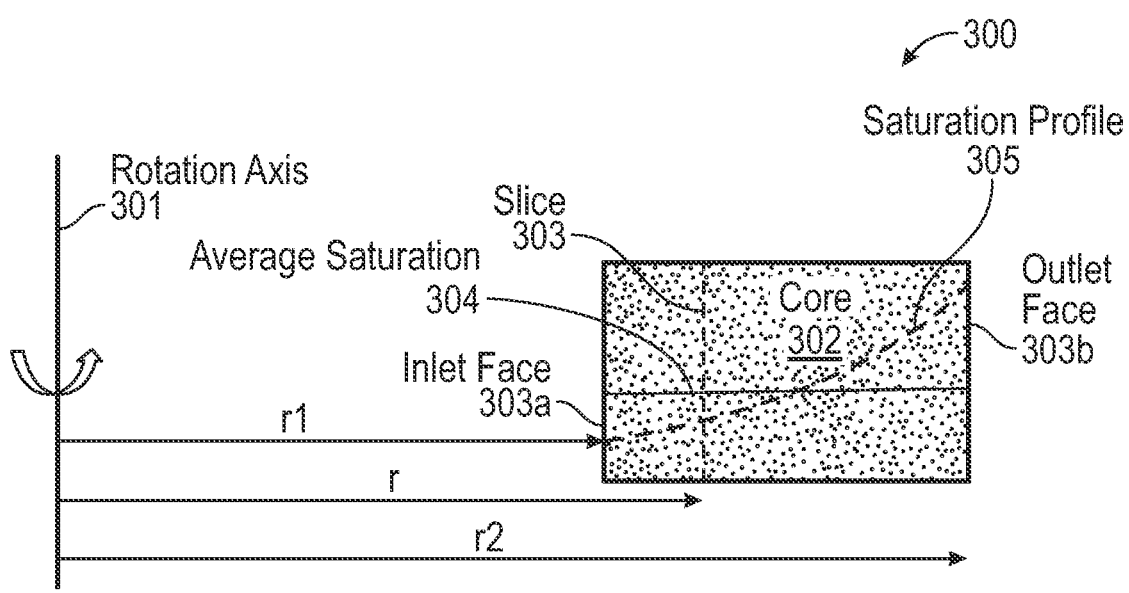

Turning to FIG. 3, FIG. 3 shows a schematic diagram in accordance with one or more embodiments. In one or more embodiments, one or more of the modules and/or elements shown in FIG. 3 may be omitted, repeated, and/or substituted. Accordingly, embodiments of the invention should not be considered limited to the specific arrangements of modules and/or elements shown in FIG. 3.

As shown in FIG. 3, FIG. 3 illustrates a centrifuge (300), which is a piece of equipment that secures the core (302) in a sample holder where the sample holder rotates around the rotation axis (301) at a controlled rotational speed. The core (302) is an example of the core sample described in reference to FIGS. 1 and 2 above. In the centrifuge (300), the distance from the rotation axis (301) to the nearest surface of the core (302) (i.e., the inlet face (303a)) is denoted as r1, and the distance from the rotation axis (301) to the farthest surface of the core (302) (i.e., the outlet face (303b)) is denoted as r2. In one example configuration, the length of the core (302) (i.e., difference between r2 and r1) is substantially less than (e.g., <10%) the distance r2 or r1. For the purpose of recording the capillary pressure curve, the centrifugal force at a particular rotational speed is approximately the same throughout the core (302). Through multiple rotation sessions of the centrifuge (300), the core (302) is rotated at successively incremented rotational speeds such that multiple levels of centrifugal force are successively applied to the core (302). Subsequent to each rotation session, the average saturation (304) is measured as an indication of the amount of fluid remaining in the core (302). In such configuration, the capillary pressure curve is recorded based on multiple successive rotation sessions of the centrifuge (300) at multiple rotational speeds.

In another example configuration, the length of the core (302) (i.e., difference between r2 and r1) is a large portion (e.g., >10%) of the distance r2 or r1. For the purpose of recording the capillary pressure curve, the centrifugal force increases from the inlet face (303a) to the outlet face (303b). Within a slice (e.g., slice (303)) of the core (302), the centrifugal force is approximated as a constant. A slice is a cross-section of the core (302) having a thickness substantially smaller than (e.g., <10%) the distance r2 or r1. For example, the centrifugal force exerted to the slice (303) is related to the rotational speed of the centrifuge (300) by the equation below:

$$F_c = m\omega^2 r \qquad \text{Eq. (2)}$$

In the equation Eq. (2), $F_c$ denotes the centrifugal force, m denotes the mass of the slice (303), ω denotes the angular rotational speed, and r denotes the distance of the slice (303) from the rotational axis (301). According to the equation Eq(2), increasing levels of centrifugal force are applied to successive slices of the core (302). Subsequent to a single rotation session, the saturation profile (305) is measured as an indication of the amount of fluid remaining in the core (302). The saturation profile is a set of recorded data that specifies a saturation measure for each slice in the core sample. Because a range of saturation measurements are recorded in the saturation profile (305) corresponding to successively increasing centrifugal force levels, the capillary pressure curve is recorded based on a single rotation session of the centrifuge (300) at a single rotational speed.

Methods to obtain pore size distribution from capillary pressure curve may assume that fluid films formed on rough surfaces in large pores have negligible volume compared to the volume of these large pores. If significant amount of fluid exists as films on the rough pore surfaces, the pore size distribution generated based on the assumption above will be largely incorrect. In one or more embodiments, the fluid film formed on rough pore surfaces are excluded from the saturation profile measurements to generate accurate pore size distribution. Throughout this disclosure, the term "pore surface" refers to the interior surface inside the pore volume. Details of excluding the fluid film from the saturation profile are described below.

Figure 4:
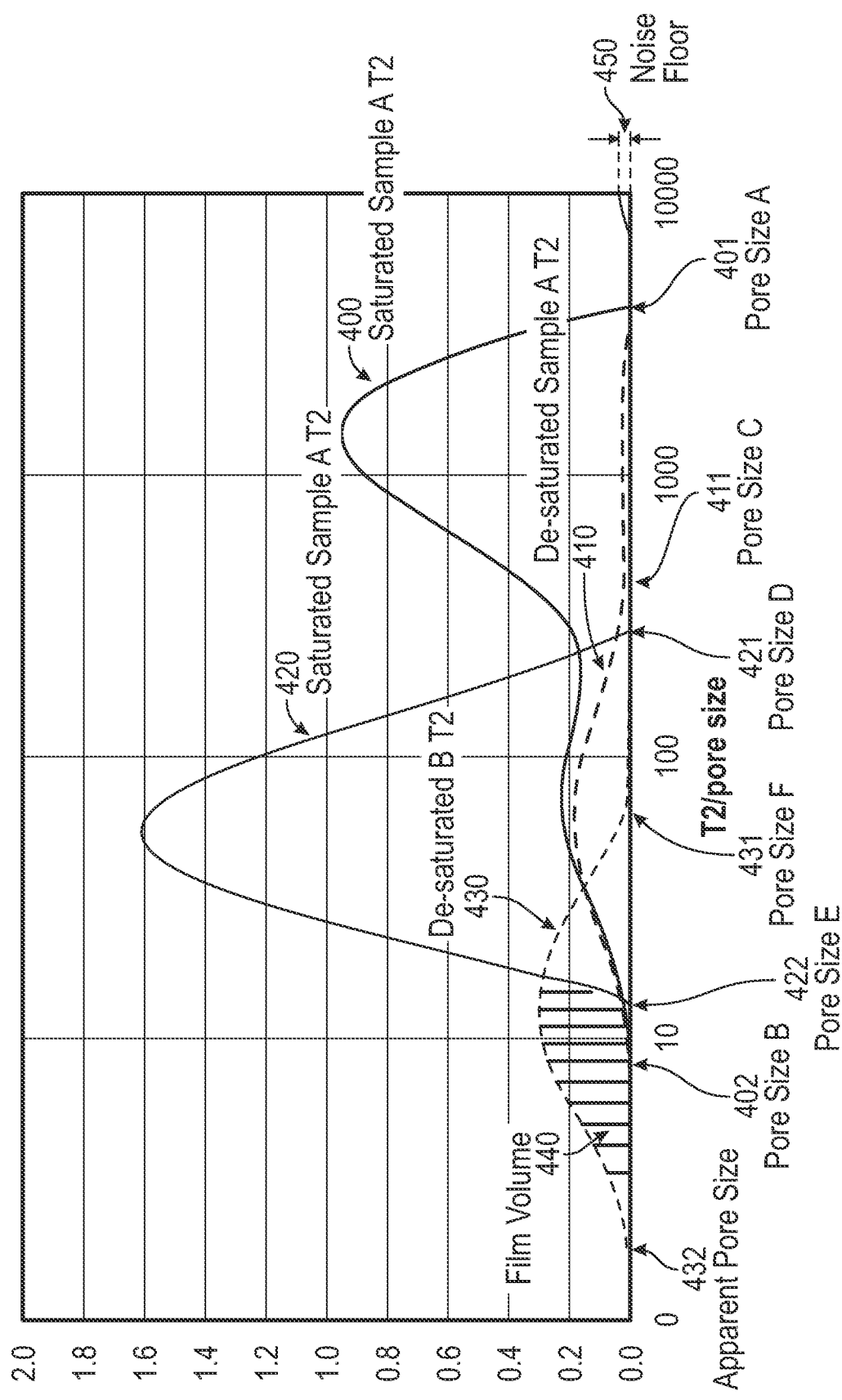

Turning to FIG. 4, FIG. 4 shows a NMR transverse relaxation time (T2) distribution diagram in accordance with one or more embodiments. In one or more embodiments, one or more of the modules and/or elements shown in FIG. 4 may be omitted, repeated, and/or substituted. Accordingly, embodiments of the invention should not be considered limited to the specific arrangements of modules and/or elements shown in FIG. 4.

As shown in FIG. 4, FIG. 4 illustrates NMR T2 distributions of a sample A and a sample B in both a saturated state and a de-saturated state. The horizontal axis of the distribution diagram represents the transverse relaxation time (T2) of the NMR measurements and the vertical axis of the distribution diagram represents signal magnitude (referred to as T2 magnitude) of the NMR measurements. In particular, the saturated sample A T2 (400) is the T2 distribution of the sample A that is saturated with a fluid (e.g., brine), and the de-saturated sample A T2 (410) is the T2 distribution of the sample A that is de-saturated by the aforementioned external force applied to the core sample, e.g., through a rotation session in the centrifuge (300). The saturated sample B T2 (420) is the T2 distribution of the sample B that is saturated with the fluid (e.g., brine), and the de-saturated sample B T2 (430) is the T2 distribution of the sample B that is de-saturated by the aforementioned external force applied to the core sample, e.g., through a rotation session in the centrifuge (300). In one or more embodiments, the sample A and/or the sample B correspond to the core sample that is measured using the porous plate method, the centrifuge method, or the mercury injection method. For example, the de-saturated T2 distribution may correspond to any one of the successively incremented external force levels applied in the porous plate method, the centrifuge method, or the mercury injection method. In one or more embodiments, the sample A and/or the sample B correspond to one or more slices in the core (320) depicted in FIG. 3 above.

Based on the NMR method, the T2 distribution of a fluid in porous media is given as the following equation:

$$\frac{1}{T_2} = \frac{1}{T_{2bulk}} + \frac{1}{T_{2surface}} + \frac{1}{T_{2diffusion}} \approx \rho_2 \left(\frac{S}{V}\right)_{pore} \quad \text{Eq. (3)}$$

In the equation Eq. (3), $\rho_2$ denotes surface relaxivity, $$\left(\frac{S}{V}\right)_{pore}$$

denotes the ratio of pore surface to fluid volume. The bulk and diffusion terms can be ignored in the laboratory measurement, and S/V is a measurement of pore size. For a spherical pore, S/V equals to 3/R where R is the radius of the spherical pore. When the rock is 100% saturated, the T2 distribution can be converted to pore size distribution using the equation Eq. (3) if surface relaxivity is known. Note that the pore size is the size of pore body instead of pore throat.

Based on the correspondence between T2 and pore size described above, the horizontal axis of the T2 distribution diagram also represents the pore size in the core sample. The NMR measurements in the T2 distribution include contributions from all fluid containing pores in the core sample. Because the sample A is fully saturated, the saturated sample A T2 (400) includes contributions from all pores of the core sample. The largest T2 value (i.e., longest transverse relaxation time) of the saturated sample A T2 (400) corresponds to the pore size A (401) and is the largest pore size in the sample A. The smallest T2 value (i.e., shortest transverse relaxation time) of the saturated sample A T2 (400) corresponds to the pore size B (402) and is the smallest pore size in the sample A. The largest and the smallest T2 values correspond to the horizontal intercepts of the T2 distribution excluding any contributions from the noise floor (450) of the NMR measurements. Subsequent to applying one of the successively incremented external force levels to incrementally de-saturate the sample A, the fluid is expelled from larger pores in the sample A. This is because smaller pores require greater external force to counterbalance the capillary pressure to relinquish the contained fluid. The largest T2 value (i.e., longest transverse relaxation time) of the de-saturated sample A T2 (410) corresponds to the pore size C (411) and is the largest pore size still containing fluid in the de-saturated sample A. The de-saturated sample A T2 (410) and the saturated sample A T2 (400) have the same smallest T2 value (i.e., shortest transverse relaxation time) that corresponds to the pore size B (402). This is because the sample A, whether in the saturated state or the de-saturated state, does not have any pores having size smaller than the pore size B (402). The integral (i.e., cumulative area) of the saturated sample A T2 (400) with respect to the horizontal axis represents a saturation measure of the sample A, i.e., the amount of the fluid stored in the pores of the sample A in the saturated state. Similarly, the integral of the de-saturated sample A T2 (410) with respect to the horizontal axis represents the saturation measure of the sample A in the de-saturated state, i,e, the amount of the fluid stored in the pores of the sample A in the de-saturated state. The saturation measure difference between the saturated state and the de-saturated state is a measure of the amount of fluid expelled from the sample A (i.e., the expelled amount) up to the current de-saturated state. The aforementioned capillary pressure curve of the sample A may be generated by successively recording the saturation measure difference between the saturated state and the de-saturated state after applying each successively incremented external force level. The saturation measure difference corresponds to the area between the solid curve and the dotted curve, as determined by subtracting the integral of the de-saturated sample A T2 (410) from the integral of the saturated sample A T2 (400).

The capillary pressure curve of the sample A may be generated by successively recording the area after applying each successively incremented external force level.

Similar to the sample A, the largest T2 value (i.e., longest transverse relaxation time) of the saturated sample B T2 (420) corresponds to the pore size D (421) and is the largest pore size in the sample B. The smallest T2 value (i.e., shortest transverse relaxation time) of the saturated sample B T2 (420) corresponds to the pore size E (422) and is the smallest pore size in the sample B. Subsequent to applying one of the successively incremented external force levels to incrementally de-saturate the sample B, the fluid is expelled from larger pores in the sample B in the same way as the sample A. The largest T2 value (i.e., longest transverse relaxation time) of the de-saturated sample B T2 (430) corresponds to the pore size F (431) and is the largest pore size still containing fluid in the de-saturated sample B. In contrast to the de-saturated sample A, the de-saturated sample B T2 (430) and the saturated sample B T2 (420) have the different smallest T2 values (i.e., shortest transverse relaxation time). Specifically, the smallest T2 value (i.e., shortest transverse relaxation time) of the de-saturated sample B T2 (430) corresponds to the apparent pore size (432) and is smaller than the pore size E (422). The apparent pore size (432) corresponds to rough surfaces in the larger pores where the fluid has been expelled except the fluid film. For example, the pores having pore sizes between the pore size D (421) and the pore size F (431) have rough pore surfaces. The irregular curvatures of these rough pore surfaces retain fluid films due to even larger surface tension than the capillary forces present in the smallest pores of the sample B (i.e., the pore size E (422)). These fluid films require even greater external force to counterbalance their surface tension to be relinquished from the rough pore surfaces in the larger pores. The amount of the fluid films retained on the rough pore surfaces in the larger pores depends on the surface area of the rough pore surface. Specifically, the amount of the fluid films corresponds to the film volume (440) and does not indicate additional pore volume. The film volume (440) is determined as the integral of the de-saturated sample B T2 (430) with respect to the portion of the horizontal axis less than the smallest T2 value (i.e., shortest transverse relaxation time) of the saturated sample B T2 (420). In other words, the film volume (440) is determined as the integral of the de-saturated sample B T2 (430) with respect to the portion of the horizontal axis between the apparent port size (432) and the port size E (422). For the purpose of determining the capillary pressure curve, any contribution from the film volume (440) is excluded when successively recording the saturation measure after applying each successively incremented external force level.

The significant film volume of certain rocks (e.g., low permeability carbonate rocks such as rocks from Shuaiba region) potentially affects the accuracy of all three capillary pressure and pore size distribution methods (i.e. porous plate, centrifuge, and mercury injection methods). The outcome of this inaccuracy depends on the applications of capillary pressures. An improved centrifuge method, based on NMR saturation profile with film volume correction is described in reference to FIGS. 5 and 6 below. The porous plate method and the mercury injection method may also be improved by using NMR measurements with film volume correction. For example, the expelled fluid volume and/or retained fluid volume may be determined based on the NMR measurements with film volume correction instead of physically collecting and measuring the expelled fluid. Accordingly, the improved porous plate, centrifuge, and mercury injection methods provide the benefits of shorter measurement time to generate more accurate results.

Figure 5:
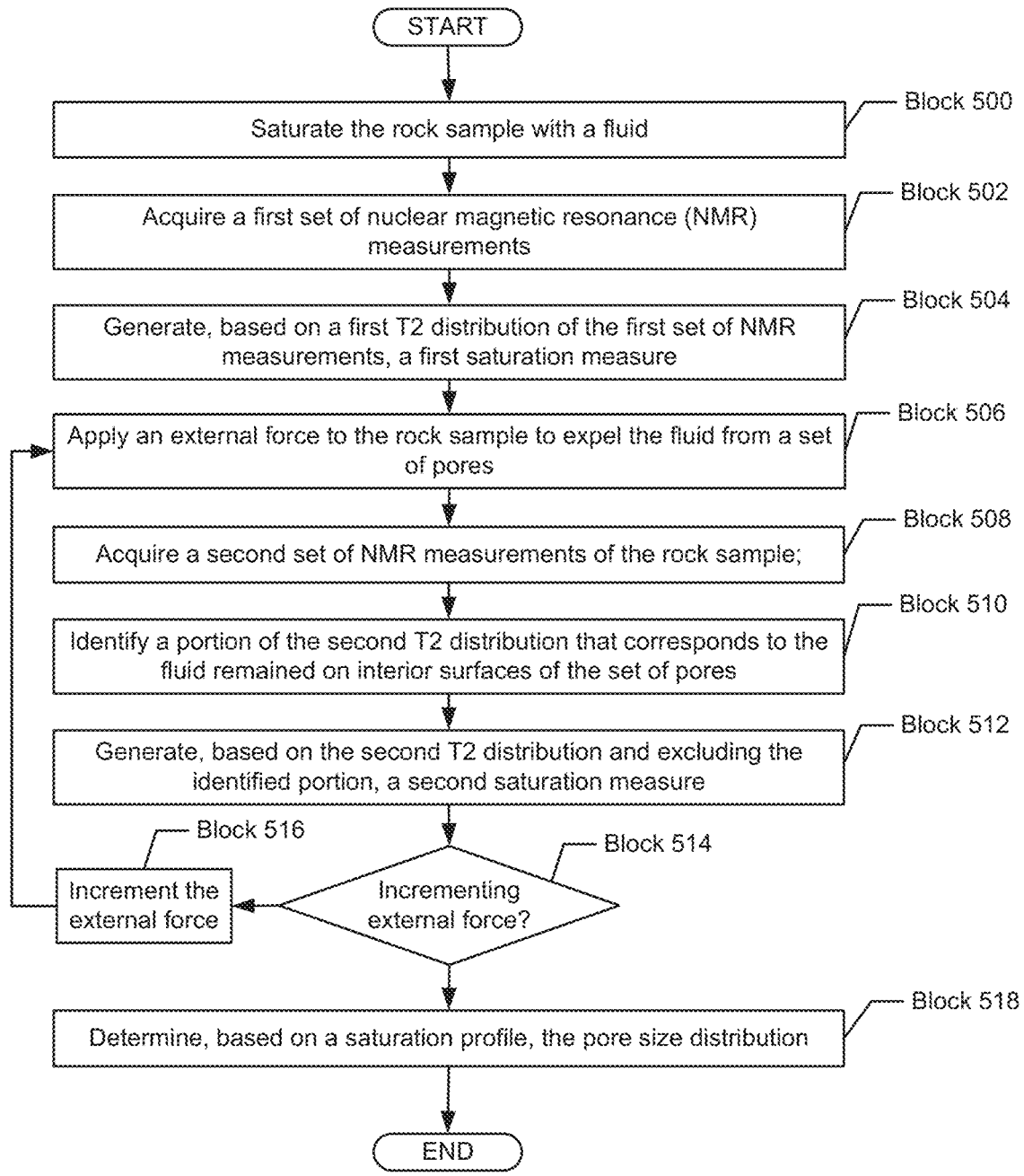
FIG. 5 shows a flowchart in accordance with one or more embodiments.

Turning to FIG. 5, FIG. 5 shows a flowchart in accordance with one or more embodiments. Specifically, FIG. 5 describes a method for determining the pore size distribution of reservoir rocks having rough pore surfaces. One or more blocks in FIG. 5 may be performed using one or more components (e.g., reservoir simulator (160), capillary bundle model (200), centrifuge (300)) as described in FIGS. 1, 2, 3, and 4. While the various blocks in FIG. 5 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

Initially in Block 500, a rock sample is saturated with a fluid. The rock sample may be a core sample obtained from the reservoir by drilling. The rock sample represents characteristics of the reservoir rocks. The fluid may be a brine solution.

In Block 502, a first set of nuclear magnetic resonance (NMR) measurements of the rock sample is acquired.

In Block 504, a first saturation measure is generated based on a first T2 distribution of the first set of NMR measurements. The T2 distribution is generated by inversion of the first set of NMR measurements. The first saturation measure represents an initial amount of the fluid stored in the rock sample that is measured as a percentage, a ratio, a value with a physical unit, or other suitable formats. In one or more embodiments, the first saturation measure is generated by computing an integral of the first T2 distribution with respect to the transverse relaxation time.

In Block 506, subsequent to acquiring the first set of NMR measurements, an external force is applied to the rock sample to expel the fluid from the rock sample. The first external force exceeds a capillary pressure of a first set of pores of the rock sample. Accordingly, the fluid is expelled from the first set of pores. For example, in the porous plate method, gas pressure is applied as the external force to press the saturated rock sample against a porous plate. In the centrifuge method, the external force is the centrifugal force created by spinning the saturated rock sample around a rotation axis. In the mercury injection method, the external force is the pressure that forces the mercury to enter the saturated rock sample.

In Block 508, subsequent to applying the first external force, a second set of NMR measurements of the rock sample is acquired.

In Block 510, by comparing a second T2 distribution of the second set of NMR measurements and the first T2 distribution, a portion of the second T2 distribution is identified that corresponds to the fluid remaining on interior surfaces of the first set of pores. A surface tension of the fluid on the interior surfaces exceeds the external force to retain the fluid as a film on the interior surfaces. The surface tension is based on an interior surface roughness of the first set of pores. In one or more embodiments, the portion of the second T2 distribution is identified based on a shortest transverse relaxation time of the first T2 distribution. In one or more embodiments, based on the identified portion of the second T2 distribution, a film volume is generated that represents an estimated amount of the fluid remaining on the interior surfaces of the first set of pores.

In Block 512, a second saturation measure of the rock sample is generated based on the second T2 distribution and excluding the identified portion. The second saturation measure represents a remaining amount of the fluid remained in a second set of pores of the rock sample. The second set of pores are smaller than the first set of pores. The capillary pressure of the second set of pores exceeds the applied external force to retain the fluid in the second set of pores. In one or more embodiments, the second saturation measure is generated by computing a the integral of the second T2 distribution with respect to the transverse relaxation time where the integral excludes any contribution from the identified portion that corresponds to the retained fluid films. For example, the film volume may be subtracted when computing the integral.

In Block 514, a determination is made as to whether to increment the external force to generate additional saturation measures to complete a saturation profile. If the determination is positive, the method proceeds to Block 516 where the external force is incremented before the method returns to Block 506. If the determination is negative, the method proceeds to Block 518. Through the iterations of Block 506 to Block 516, the saturation profile is generated by recording the saturation measures with respect to incrementing levels of the external forces. In each iteration, the external force is counterbalanced by the capillary pressure and the recorded saturation profile may be used to derive the aforementioned capillary pressure curve.

In Block 516, the pore size distribution is determined based at least on the saturation profile. In one or more embodiments, a tally of the first set of pores is determined by at least comparing the first saturation measure and the second saturation measure. In particular, the difference between the first saturation measure and the second saturation measure corresponds to the difference between the initial amount of fluid in the rock sample and the remaining amount of the fluid after applying the external force. In other words, the difference represents the amount of the fluid expelled from the first set of pores, i.e., a volume of the first set of pores. As noted above, the capillary pressure of the first set of pores is counterbalanced by the external force. The pore size of the first set of pores is determined based on the external force using the equation Eq. (1). The tally of pores is then computed by dividing the volume of the first set of pores by the pore size. The pore size of the first set of pores and the corresponding tally is included in the pore size distribution. Additional tallies in the pore size distribution is generated in the same fashion based on the saturation measures generated in subsequent iterations.

Figure 6:
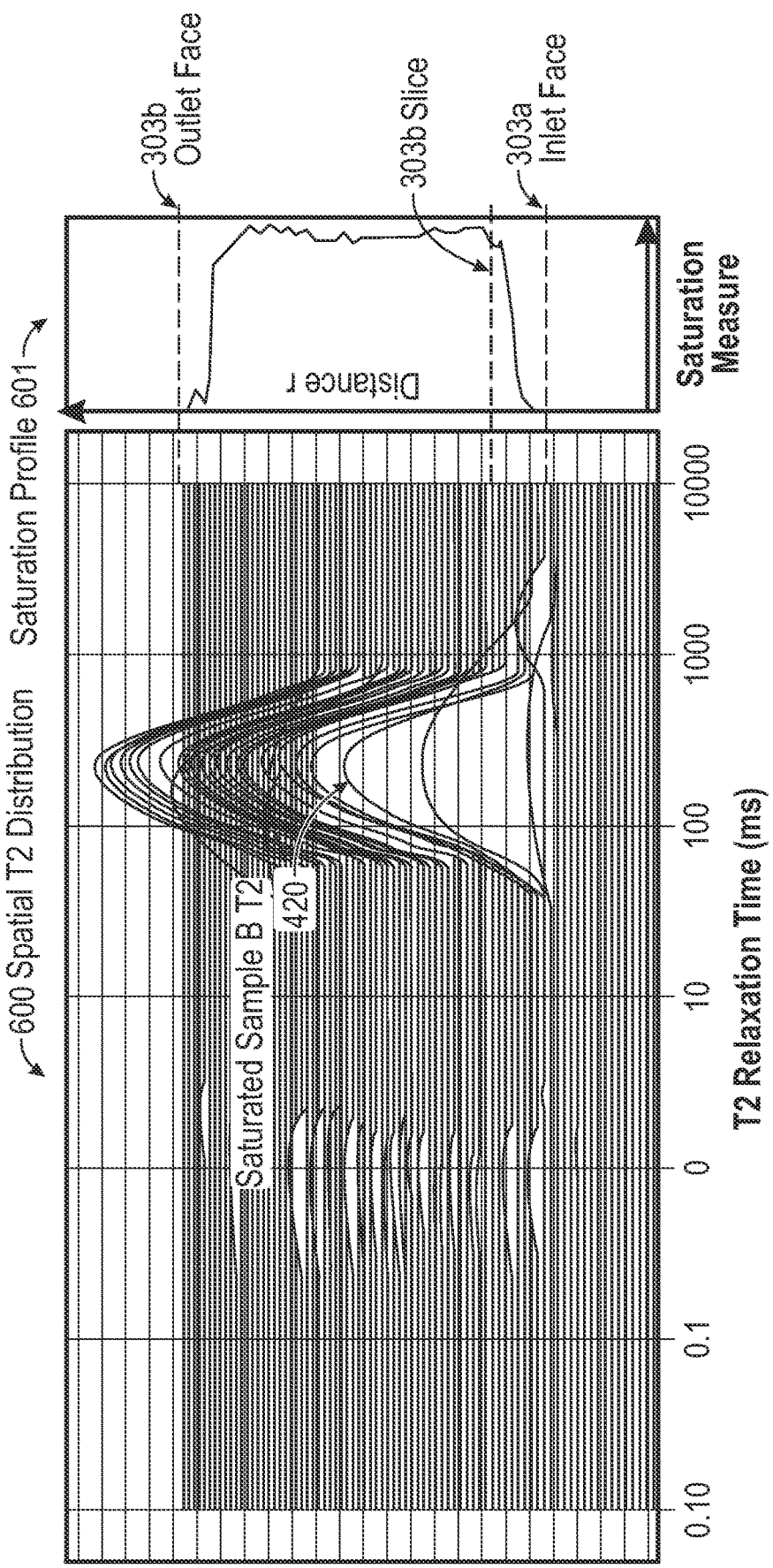
FIG. 6 shows an example in accordance with one or more embodiments.

Turning to FIG. 6, FIG. 6 provides an example of an improved centrifuge method using a single rotational speed. The example shown in FIG. 6 may be, for example, based on one or more components depicted in FIGS. 1-4 above and the method flowchart depicted in FIG. 5 above. In one or more embodiments, one or more of the modules and/or elements shown in FIG. 6 may be omitted, repeated, and/or substituted. Accordingly, embodiments of the invention should not be considered limited to the specific arrangements of modules and/or elements shown in FIG. 6.

Turning to FIG. 6, FIG. 6 illustrates a spatial T2 distribution (600) and a saturation profile (601), e.g., of the core (302) that are generated using the centrifuge (300) depicted in FIG. 3 above. The saturation profile (601) is a plot of saturation measures as a function of distance from rotation axis (301). The saturation profile (601) includes a range from the inlet face (303a) to the outlet face (303b) through the length of the core (302). The spatial T2 distribution (600) is the collection of T2 distributions that are individually inverted from the NMR measurements of successive thin slices of the core (302). As described in reference to FIG. 4 above, the saturation measure is the integral of T2 amplitudes in the T2 distribution of each slice. For example, the spatial T2 distribution (600) and the saturation profile (601) may correspond to the saturated state of the sample B depicted in FIG. 4 above. In particular, the saturated sample B T2 (420) is measured on the slice (303) and is drawn in the spatial T2 distribution (600) at the corresponding location of the slice (303) in the saturation profile (601).

After centrifuge spinning the core (302) at a single speed in the centrifuge (300), the T2 distribution of each slice is similar to dotted curves shown in FIG. 3. Any significant film volume (e.g., film volume (440)) is separated from the small pore volume still retaining fluid after the centrifuge spinning. The film volume is excluded from computing the integral of the T2 amplitudes to determine the saturation measure of the de-saturated sample B. The new saturation profile of the de-saturated sample B excluding contributions from the film volume is then used to calculate the capillary pressure curve for determining accurate pore size distribution. Based on the description above, TABLE 1 shows an example workflow for the improved centrifuge method using a single rotational speed to generate the capillary pressure curve and pore size distribution.

TABLE 1

| Step 1. | Saturate the rock sample with brine |
| Step 2. | Measure T2, saturation profile, and spatial T2 |
| Step 3. | Spin the sample in the centrifuge |
| Step 4. | Measure the T2, saturation profile, and spatial T2 |
| Step 5. | Compare the T2 at 100% saturated and desaturated states for film volume estimation |
| Step 5. | If the film volume is negligible, calculate the capillary pressure using saturation profiles |
| Step 6. | If the film volume is not negligible, correct the saturation profiles by subtracting the film volume, and calculate the capillary pressure using corrected saturation profiles. |
| Step 7. | Go to Step 3 to spin the sample for next speed in the centrifuge. |

Figure 7A:
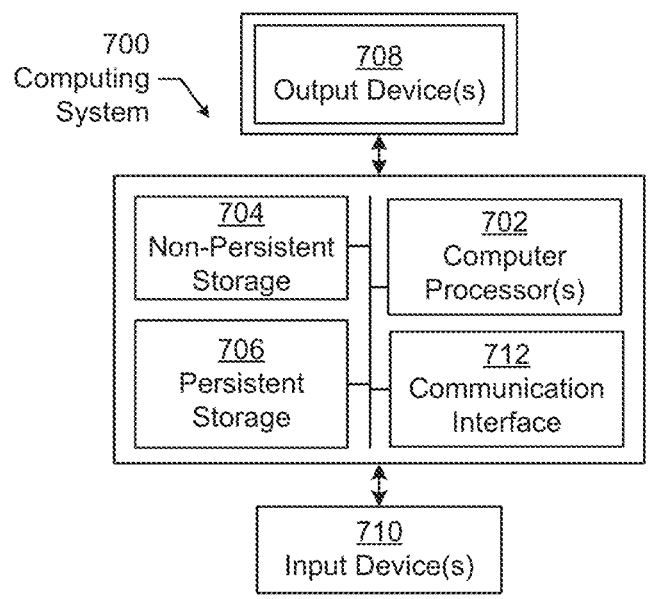
FIGS. 7A and 7B show a computing system in accordance with one or more embodiments.

Embodiments may be implemented on a computing system. Any combination of mobile, desktop, server, router, switch, embedded device, or other types of hardware may be used. For example, as shown in FIG. 7A, the computing system (800) may include one or more computer processors (802), non-persistent storage (804) (e.g., volatile memory, such as random access memory (RAM), cache memory), persistent storage (806) (e.g., a hard disk, an optical drive such as a compact disk (CD) drive or digital versatile disk (DVD) drive, a flash memory, etc.), a communication interface (812) (e.g., Bluetooth interface, infrared interface, network interface, optical interface, etc.), and numerous other elements and functionalities.

The computer processor(s) (802) may be an integrated circuit for processing instructions. For example, the computer processor(s) may be one or more cores or micro-cores of a processor. The computing system (800) may also include one or more input devices (810), such as a touchscreen, keyboard, mouse, microphone, touchpad, electronic pen, or any other type of input device.

The communication interface (812) may include an integrated circuit for connecting the computing system (800) to a network (not shown) (e.g., a local area network (LAN), a wide area network (WAN) such as the Internet, mobile network, or any other type of network) and/or to another device, such as another computing device.

Further, the computing system (800) may include one or more output devices (808), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (802), non-persistent storage (804), and persistent storage (806). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

Figure 7B:
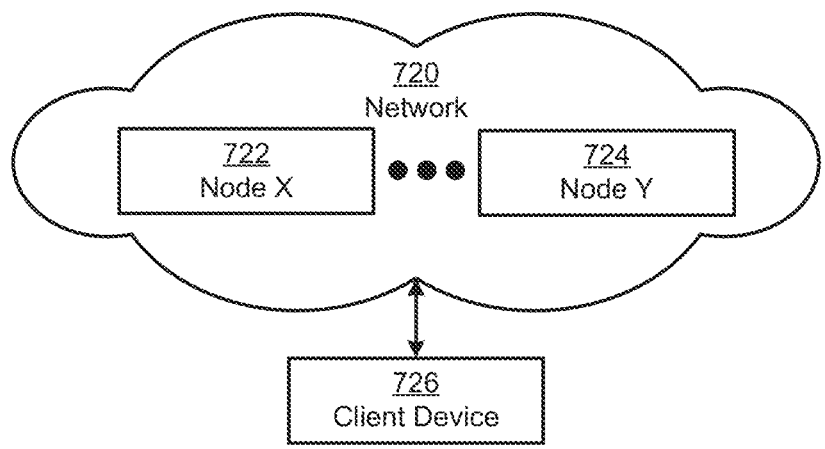

The computing system (800) in FIG. 7A may be connected to or be a part of a network. For example, as shown in FIG. 7B, the network (820) may include multiple nodes (e.g., node X (822), node Y (824)). Each node may correspond to a computing system, such as the computing system shown in FIG. 7A, or a group of nodes combined may correspond to the computing system shown in FIG. 7A. By way of an example, embodiments of the disclosure may be implemented on a node of a distributed system that is connected to other nodes. By way of another example, embodiments of the disclosure may be implemented on a distributed computing system having multiple nodes, where each portion of the disclosure may be located on a different node within the distributed computing system. Further, one or more elements of the aforementioned computing system (800) may be located at a remote location and connected to the other elements over a network.

Although not shown in FIG. 7B, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (e.g., node X (822), node Y (824)) in the network (820) may be configured to provide services for a client device (826). For example, the nodes may be part of a cloud computing system. The nodes may include functionality to receive requests from the client device (826) and transmit responses to the client device (826). The client device (826) may be a computing system, such as the computing system shown in FIG. 7A. Further, the client device (826) may include and/or perform all or a portion of one or more embodiments of the disclosure.

The computing system or group of computing systems described in FIGS. 7A and 7B may include functionality to perform a variety of operations disclosed herein. For example, the computing system(s) may perform communication between processes on the same or different systems. A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided below.

Based on the client-server networking model, sockets may serve as interfaces or communication channel endpoints enabling bidirectional data transfer between processes on the same device. Foremost, following the client-server networking model, a server process (e.g., a process that provides data) may create a first socket object. Next, the server process binds the first socket object, thereby associating the first socket object with a unique name and/or address. After creating and binding the first socket object, the server process then waits and listens for incoming connection requests from one or more client processes (e.g., processes that seek data). At this point, when a client process wishes to obtain data from a server process, the client process starts by creating a second socket object. The client process then proceeds to generate a connection request that includes at least the second socket object and the unique name and/or address associated with the first socket object. The client process then transmits the connection request to the server process. Depending on availability, the server process may accept the connection request, establishing a communication channel with the client process, or the server process, busy in handling other operations, may queue the connection request in a buffer until the server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (e.g., bytes).

Shared memory refers to the allocation of virtual memory space in order to substantiate a mechanism for which data may be communicated and/or accessed by multiple processes. In implementing shared memory, an initializing process first creates a shareable segment in persistent or non-persistent storage. Post creation, the initializing process then mounts the shareable segment, subsequently mapping the shareable segment into the address space associated with the initializing process. Following the mounting, the initializing process proceeds to identify and grant access permission to one or more authorized processes that may also write and read data to and from the shareable segment. Changes made to the data in the shareable segment by one process may immediately affect other processes, which are also linked to the shareable segment. Further, when one of the authorized processes accesses the shareable segment, the shareable segment maps to the address space of that authorized process. Often, one authorized process may mount the shareable segment, other than the initializing process, at any given time.

Other techniques may be used to share data, such as the various data described in the present application, between processes without departing from the scope of the disclosure. The processes may be part of the same or different application and may execute on the same or different computing system.

Rather than or in addition to sharing data between processes, the computing system performing one or more embodiments of the disclosure may include functionality to receive data from a user. For example, in one or more embodiments, a user may submit data via a graphical user interface (GUI) on the user device. Data may be submitted via the graphical user interface by a user selecting one or more graphical user interface widgets or inserting text and other data into graphical user interface widgets using a touchpad, a keyboard, a mouse, or any other input device. In response to selecting a particular item, information regarding the particular item may be obtained from persistent or non-persistent storage by the computer processor. Upon selection of the item by the user, the contents of the obtained data regarding the particular item may be displayed on the user device in response to the user's selection.

By way of another example, a request to obtain data regarding the particular item may be sent to a server operatively connected to the user device through a network. For example, the user may select a uniform resource locator (URL) link within a web client of the user device, thereby initiating a Hypertext Transfer Protocol (HTTP) or other protocol request being sent to the network host associated with the URL. In response to the request, the server may extract the data regarding the particular selected item and send the data to the device that initiated the request. Once the user device has received the data regarding the particular item, the contents of the received data regarding the particular item may be displayed on the user device in response to the user's selection. Further to the above example, the data received from the server after selecting the URL link may provide a web page in Hyper Text Markup Language (HTML) that may be rendered by the web client and displayed on the user device.

Once data is obtained, such as by using techniques described above or from storage, the computing system, in performing one or more embodiments of the disclosure, may extract one or more data items from the obtained data. For example, the extraction may be performed as follows by the computing system (800) in FIG. 7A. First, the organizing pattern (e.g., grammar, schema, layout) of the data is determined, which may be based on one or more of the following: position (e.g., bit or column position, Nth token in a data stream, etc.), attribute (where the attribute is associated with one or more values), or a hierarchical/tree structure (consisting of layers of nodes at different levels of detail—such as in nested packet headers or nested document sections). Then, the raw, unprocessed stream of data symbols is parsed, in the context of the organizing pattern, into a stream (or layered structure) of tokens (where each token may have an associated token "type").

Next, extraction criteria are used to extract one or more data items from the token stream or structure, where the extraction criteria are processed according to the organizing pattern to extract one or more tokens (or nodes from a layered structure). For position-based data, the token(s) at the position(s) identified by the extraction criteria are extracted. For attribute/value-based data, the token(s) and/or node(s) associated with the attribute(s) satisfying the extraction criteria are extracted. For hierarchical/layered data, the token(s) associated with the node(s) matching the extraction criteria are extracted. The extraction criteria may be as simple as an identifier string or may be a query presented to a structured data repository (where the data repository may be organized according to a database schema or data format, such as XML).

The extracted data may be used for further processing by the computing system. For example, the computing system of FIG. 7A, while performing one or more embodiments of the disclosure, may perform data comparison. Data comparison may be used to compare two or more data values (e.g., A, B). For example, one or more embodiments may determine whether $A>B$, $A=B$, $A \mathrel{!}= B$, $A<B$, etc. The comparison may be performed by submitting A, B, and an opcode specifying an operation related to the comparison into an arithmetic logic unit (ALU) (i.e., circuitry that performs arithmetic and/or bitwise logical operations on the two data values). The ALU outputs the numerical result of the operation and/or one or more status flags related to the numerical result. For example, the status flags may indicate whether the numerical result is a positive number, a negative number, zero, etc. By selecting the proper opcode and then reading the numerical results and/or status flags, the comparison may be executed. For example, in order to determine if $A>B$, B may be subtracted from A (i.e., A−B), and the status flags may be read to determine if the result is positive (i.e., if $A>B$, then $A-B>0$). In one or more embodiments, B may be considered a threshold, and A is deemed to satisfy the threshold if $A=B$ or if $A>B$, as determined using the ALU. In one or more embodiments of the disclosure, A and B may be vectors, and comparing A with B includes comparing the first element of vector A with the first element of vector B, the second element of vector A with the second element of vector B, etc. In one or more embodiments, if A and B are strings, the binary values of the strings may be compared.

The computing system in FIG. 7A may implement and/or be connected to a data repository. For example, one type of data repository is a database. A database is a collection of information configured for ease of data retrieval, modification, re-organization, and deletion. Database Management System (DBMS) is a software application that provides an interface for users to define, create, query, update, or administer databases.

The user, or software application, may submit a statement or query into the DBMS. Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g. join, full join, count, average, etc.), sort (e.g. ascending, descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The computing system of FIG. 7A may include functionality to present raw and/or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Data may also be presented through various audio methods. In particular, data may be rendered into an audio format and presented as sound through one or more speakers operably connected to a computing device.

Data may also be presented to a user through haptic methods. For example, haptic methods may include vibrations or other physical signals generated by the computing system. For example, data may be presented to a user using a vibration generated by a handheld computer device with a predefined duration and intensity of the vibration to communicate the data.

The above description of functions presents only a few examples of functions performed by the computing system of FIG. 7A and the nodes and/or client device in FIG. 7B. Other functions may be performed using one or more embodiments of the disclosure.

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure should be limited only by the attached claims.

Although the preceding description has been described herein with reference to particular means, materials and embodiments, it is not intended to be limited to the particulars disclosed herein; rather, it extends to all functionally equivalent structures, methods and uses, such as are within the scope of the appended claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed is:

1. A method for determining a pore size distribution in a rock sample, the method comprising:
    saturating the rock sample with a fluid;
    acquiring a first set of nuclear magnetic resonance (NMR) measurements of the rock sample;
    generating, by a computer processor and based on a first T2 distribution of the first set of NMR measurements, a first saturation measure, the first saturation measure representing an initial amount of the fluid stored in the rock sample;
    applying, subsequent to acquiring the first set of NMR measurements, a first external force to the rock sample to expel the fluid from a first plurality of pores of the rock sample;
    acquiring, subsequent to applying the first external force, a second set of NMR measurements of the rock sample;
    identifying, by the computer processor based on comparing a second T2 distribution of the second set of NMR measurements and the first T2 distribution, a portion of the second T2 distribution that corresponds to the fluid remaining on interior surfaces of the first plurality of pores;
    generating, by the computer processor and based on the second T2 distribution and excluding the identified portion, a second saturation measure of the rock sample, the second saturation measure representing a remaining amount of the fluid remained in a second plurality of pores of the rock sample; and
    determining, by the computer processor and based at least on the first saturation measure and the second saturation measure, the pore size distribution.

2. The method according to claim 1, further comprising:
    determining, by at least comparing the first saturation measure and the second saturation measure, a first tally of the first plurality of pores; and
    determining, based at least on the first centrifuge force, a first capillary pressure representing a first pore size of the first plurality of pores,
    wherein the first external force exceeds the first capillary pressure to expel the fluid from the first plurality of pores, and
    wherein determining the pore size distribution is based at least on the first tally and the first pore size.

3. The method according to claim 2,
    wherein a surface tension exceeds the first external force to retain the fluid on the interior surfaces of the first plurality of pores, the surface tension being based on an interior surface roughness of the first plurality of pores,
    wherein the second plurality of pores are smaller than the pore size of the first plurality of pores, and
    wherein a second capillary pressure of the second plurality of pores exceeds the first external force to retain the fluid in the second plurality of pores.

4. The method according to claim 3, further comprising:
    applying, subsequent to acquiring the second set of NMR measurements, a second external force to expel the fluid from a third plurality of pores of the rock sample;
    acquiring, subsequent to applying the second external force, a third set of NMR measurements of the rock sample;
    determining, based on the third set of NMR measurements and the second external force, a second tally of the third plurality of pores and a second capillary pressure representing a second pore size of the third plurality of pores,
    wherein determining the pore size distribution is further based on the second tally and the second pore size.

5. The method according to claim 1,
    wherein the portion of the second T2 distribution is identified based on a shortest transverse relaxation time of the first T2 distribution.

6. The method according to claim 1, further comprising:
    generating, based on the identified portion of the second T2 distribution, a film volume representing an estimated amount of the fluid remaining on interior surfaces of the first plurality of pores,
    wherein generating the second saturation measure comprises excluding any contribution from the film volume.

7. The method according to claim 6,
    wherein generating the first saturation measure comprises computing a first integral of the first T2 distribution, and wherein generating the second saturation measure comprises:
  computing a second integral of the second T2 distribution; and
  excluding the film volume from contributing to the second integral.

8. The method according to claim 4, further comprising:
centrifuging, using a single rotational speed, the rock sample to apply a centrifugal force to a plurality of slices of the rock sample,
wherein the first external force is the centrifugal force applied to a first slice of the plurality of slices, the first slice comprising the first plurality of pores and the second plurality of pores, the first external force being dependent on a first distance between the first slice and a rotational axis of the centrifuging, and
wherein the second external force is the centrifugal force applied to a second slice of the plurality of slices, the second slice comprising the third plurality of pores, the second external force being dependent on a second distance between the second slice and the rotational axis.

9. The method according to claim 8, further comprising:
generating, by inversion of the first set of NMR measurements, a first spatial T2 distribution comprising the first T2 distribution of the first slice;
generating, based on the first spatial T2 distribution, a first saturation profile comprising the first saturation measure, the first saturation profile representing a first distribution of the fluid stored in the plurality of slices prior to the centrifuging, the first saturation measure representing the initial amount of the fluid stored in the first slice;
generating, subsequent to the centrifuging, a second spatial T2 distribution comprising the second T2 distribution of the first slice;
generating, based on the second spatial T2 distribution, a second saturation profile comprising the second saturation measure, the second saturation profile representing a second distribution of the fluid stored in the plurality of slices subsequent to the centrifuging, the second saturation measure representing the remaining amount of the fluid stored in the first slice; and
generating, based on the first saturation profile and the second saturation profile, a capillary pressure curve representing an expelled amount of the fluid as a function of the centrifugal force applied to the plurality of slices,
wherein the pore size distribution is determined based on the capillary pressure curve.

10. A computer system for determining a pore size distribution in a rock sample, comprising:
a processor; and
a memory coupled to the processor, the memory storing instructions, when executed, comprising functionality for:
  acquiring a first set of nuclear magnetic resonance (NMR) measurements of a rock sample saturated with a fluid, wherein a first external force is applied, subsequent to acquiring the first set of NMR measurements, to the rock sample to expel the fluid from a first plurality of pores of the rock sample;
  generating, based on a first T2 distribution of the first set of NMR measurements, a first saturation measure, the first saturation measure representing an initial amount of the fluid stored in the rock sample;
  acquiring, subsequent to applying the first external force, a second set of NMR measurements of the rock sample;
  identifying, by comparing a second T2 distribution of the second set of NMR measurements and the first T2 distribution, a portion of the second T2 distribution that corresponds to the fluid remaining on interior surfaces of the first plurality of pores;
  generating, based on the second T2 distribution and excluding the identified portion, a second saturation measure of the rock sample, the second saturation measure representing a remaining amount of the fluid remained in a second plurality of pores of the rock sample; and
  determining, based at least on the first saturation measure and the second saturation measure, the pore size distribution.

11. The computer system according to claim 10, the instructions, when executed, further comprising functionality for:
  determining, by at least comparing the first saturation measure and the second saturation measure, a first tally of the first plurality of pores; and
  determining, based at least on the first centrifuge force, a first capillary pressure representing a first pore size of the first plurality of pores,
  wherein the first external force exceeds the first capillary pressure to expel the fluid from the first plurality of pores, and
  wherein determining the pore size distribution is based at least on the first tally and the first pore size.

12. The computer system according to claim 11,
wherein a surface tension exceeds the first external force to retain the fluid on the interior surfaces of the first plurality of pores, the surface tension being based on an interior surface roughness of the first plurality of pores,
wherein the second plurality of pores are smaller than the pore size of the first plurality of pores, and
wherein a second capillary pressure of the second plurality of pores exceeds the first external force to retain the fluid in the second plurality of pores.

13. The computer system according to claim 12, the instructions, when executed, further comprising functionality for:
  applying, subsequent to acquiring the second set of NMR measurements, a second external force to expel the fluid from a third plurality of pores of the rock sample;
  acquiring, subsequent to applying the second external force, a third set of NMR measurements of the rock sample;
  determining, based on the third set of NMR measurements and the second external force, a second tally of the third plurality of pores and a second capillary pressure representing a second pore size of the third plurality of pores,
  wherein determining the pore size distribution is further based on the second tally and the second pore size.

14. The computer system according to claim 10,
wherein the portion of the second T2 distribution is identified based on a shortest transverse relaxation time of the first T2 distribution.

15. The computer system according to claim 10, the instructions, when executed, further comprising functionality for:
  generating, based on the identified portion of the second T2 distribution, a film volume representing an estimated amount of the fluid remaining on interior surfaces of the first plurality of pores,
wherein generating the second saturation measure comprises excluding any contribution from the film volume.

16. The computer system according to claim 15,
wherein generating the first saturation measure comprises computing a first integral of the first T2 distribution, and
wherein generating the second saturation measure comprises:
   computing a second integral of the second T2 distribution; and
   excluding the film volume from contributing to the second integral.

17. The computer system according to claim 13, the instructions, when executed, further comprising functionality for:
   centrifuging, using a single rotational speed, the rock sample to apply a centrifugal force to a plurality of slices of the rock sample,
   wherein the first external force is the centrifugal force applied to a first slice of the plurality of slices, the first slice comprising the first plurality of pores and the second plurality of pores, the first external force being dependent on a first distance between the first slice and a rotational axis of the centrifuging, and
   wherein the second external force is the centrifugal force applied to a second slice of the plurality of slices, the second slice comprising the third plurality of pores, the second external force being dependent on a second distance between the second slice and the rotational axis.

18. The computer system according to claim 17, the instructions, when executed, further comprising functionality for:
   generating, by inversion of the first set of NMR measurements, a first spatial T2 distribution comprising the first T2 distribution of the first slice;
   generating, based on the first spatial T2 distribution, a first saturation profile comprising the first saturation measure, the first saturation profile representing a first distribution of the fluid stored in the plurality of slices prior to the centrifuging, the first saturation measure representing the initial amount of the fluid stored in the first slice;
   generating, subsequent to the centrifuging, a second spatial T2 distribution comprising the second T2 distribution of the first slice;
   generating, based on the second spatial T2 distribution, a second saturation profile comprising the second saturation measure, the second saturation profile representing a second distribution of the fluid stored in the plurality of slices subsequent to the centrifuging, the second saturation measure representing the remaining amount of the fluid stored in the first slice; and
   generating, based on the first saturation profile and the second saturation profile, a capillary pressure curve representing an expelled amount of the fluid as a function of the centrifugal force applied to the plurality of slices,
   wherein the pore size distribution is determined based on the capillary pressure curve.

19. A non-transitory computer readable medium storing instructions executable by a computer processor for determining a pore size distribution in a rock sample, the instructions, when executed by the computer processor, comprising functionality for:
   acquiring a first set of nuclear magnetic resonance (NMR) measurements of a rock sample saturated with a fluid, wherein a first external force is applied, subsequent to acquiring the first set of NMR measurements, to the rock sample to expel the fluid from a first plurality of pores of the rock sample;
   generating, based on a first T2 distribution of the first set of NMR measurements, a first saturation measure, the first saturation measure representing an initial amount of the fluid stored in the rock sample;
   acquiring, subsequent to applying the first external force, a second set of NMR measurements of the rock sample;
   identifying, by comparing a second T2 distribution of the second set of NMR measurements and the first T2 distribution, a portion of the second T2 distribution that corresponds to the fluid remaining on interior surfaces of the first plurality of pores;
   generating, based on the second T2 distribution and excluding the identified portion, a second saturation measure of the rock sample, the second saturation measure representing a remaining amount of the fluid remained in a second plurality of pores of the rock sample; and
   determining, based at least on the first saturation measure and the second saturation measure, the pore size distribution.

20. The non-transitory computer readable medium according to claim 19, the instructions, when executed by the computer processor, further comprising functionality for:
   determining, by at least comparing the first saturation measure and the second saturation measure, a first tally of the first plurality of pores; and
   determining, based at least on the first centrifuge force, a first capillary pressure representing a first pore size of the first plurality of pores,
   wherein the first external force exceeds the first capillary pressure to expel the fluid from the first plurality of pores, and
   wherein determining the pore size distribution is based at least on the first tally and the first pore size.

* * * * *